United States Patent [19]
Iwata et al.

[11] Patent Number: 5,501,965
[45] Date of Patent: Mar. 26, 1996

[54] PROCESS FOR PRODUCING FRUCTOSE 2,6-BISPHOSPHATE AND PURIFICATION PROCESS THEREOF

[75] Inventors: Ken Iwata; Tatsuo Katayama; Hiroshi Nakajima, all of Kyoto, Japan

[73] Assignee: Unitika Ltd., Hyogo, Japan

[21] Appl. No.: 213,738

[22] Filed: Mar. 16, 1994

[30] Foreign Application Priority Data

Mar. 17, 1993 [JP] Japan .................................... 5-084102
Mar. 17, 1993 [JP] Japan .................................... 5-084103

[51] Int. Cl.$^6$ ............................ C12P 19/24; C12P 19/02
[52] U.S. Cl. ................................ 435/94; 435/89; 435/92; 435/101; 435/105; 435/194; 536/125
[58] Field of Search ........................... 435/101, 194, 435/105, 94, 89, 92; 536/125

[56] References Cited

U.S. PATENT DOCUMENTS 5,094,947  3/1992  Nakajima et al. ....................... 435/105

*Primary Examiner*—Herbert J. Lilling
*Attorney, Agent, or Firm*—Sughrue, Mion, Zinn, Macpeak & Seas

[57] ABSTRACT

This invention relates to a process for the production of fructose 2,6-bisphosphate which comprises effecting reactions among (i) fructose 6-phosphate, (ii) glucose, (iii) fructose or (iv) glucose 6-phosphate, ATP and a phosphate donor, in the presence of (i) fructose 6-phosphate 2-kinase (PFK 2) and an enzyme which converts ADP into ATP (ADP/ATP converting enzyme), (ii) PFK 2, an ADP/ATP converting enzyme, hexokinase or glucokinase and glucose 6-phosphate isomerase, (iii) PFK 2, an ADP/ATP converting enzyme and hexokinase or glucokinase, or (iv) PFK 2, an ADP/ATP converting enzyme and glucose 6-phosphate isomerase; to a process for the production of fructose 2,6-bisphosphate which comprises allowing diesterase to coexist in a solution containing fructose 1,2-cyclic, 6-bisphosphate; and to a process for the purification of fructose 2,6-bisphosphate which comprises adding zinc salt to a solution containing fructose 2,6-bisphosphate, removing formed precipitate of impurities and adding a zinc salt to the resulting solution to isolate formed precipitate of fructose 2,6-bisphosphate.

According to the present invention, fructose 2,6-bisphosphate can be produced easily with a high yield and high purity fructose 2,6-bisphosphate can be obtained easily.

20 Claims, 3 Drawing Sheets

○ : Reaction 1
● : Reaction 2
▲ : Reaction 3
■ : Reaction 4
✕ : Reaction 5

5,501,965

PROCESS FOR PRODUCING FRUCTOSE 2,6-BISPHOSPHATE AND PURIFICATION PROCESS THEREOF

FIELD OF THE INVENTION

This invention relates to a process for the production of fructose 2,6-bisphosphate (to be referred to as "FBP" hereinafter) and a purification process thereof.

BACKGROUND OF THE INVENTION

In the living body, glucose metabolism is effected by the glycolytic pathway in which an enzyme called phosphofructokinase (E.C. 2.7.1.11) (to be referred to as "PFK 1" hereinafter) plays an important role as a regulatory factor. FBP is a factor which directly activates PFK 1, and carbohydrate metabolism is regulated by the activation of PFK 1. Thus, it has been confirmed in recent years that FBP plays an important role in the living body as a carbohydrate metabolism-related factor.

In general, FBP is produced either by organic synthesis or enzymatic synthesis. In the organic synthesis process, FBP is produced, for example, by firstly synthesizing fructose 1,2-cyclic, 6-bisphosphate (to be referred to as "FCP" hereinafter) from a starting material, fructose 1,6-bisphosphate (to be referred to as "FDP" hereinafter), using dicyclohexyl carbodiimide as a catalyst. The thus synthesized FCP is subjected to partial alkali hydrolysis to form FBP (E. Van Schaftingen and H. G. Hers, *European Journal of Biochemistry*, vol.117, p.319, 1981; K. Uyeda, E. Fruya and A. D. Sherry, *Journal of Biological Chemistry*, vol.256, p.8679, 1981; and JP-A-60-161994). The term "JP-A" as used herein means an "unexamined published Japanese patent application". As an example of the enzymatic synthesis method, E. Fruya and K. Uyeda (*Journal of Biological Chemistry*, vol.256, p.7109, 1981) disclose a process in which FBP is produced from fructose 6-phosphate (to be referred to as "F6P" hereinafter) and adenosine 5'-triphosphate (to be referred to as "ATP" hereinafter) by the action of fructose 6-phosphate 2-kinase (E.C. 2.7.1.105) (to be referred to as "PFK 2" hereinafter).

With regard to a process for the isolation of FBP, the present inventors are not aware of any report concerning the isolation of FBP in a high yield in the form of high purity powder. A primary reason for this is that FBP is extremely unstable in aqueous solutions especially under acidic conditions, and decomposes completely within several minutes even in a weakly acidic aqueous solution. Because of this, steps for the purification of FBP cannot be effected easily. Also, when FBP is synthesized using the aforementioned organic synthesis process, conversion ratio of FCP into FBP by hydrolysis is low (about 15%), and the isolation of FBP is quite difficult because of the extremely similar physical properties of the by-product FDP to those of the product FBP. In addition, when FBP is synthesized using the aforementioned enzymatic synthesis process, the known process is disadvantageous from a practical point of view because of the low FBP production yield.

SUMMARY OF THE INVENTION

In view of the above, an object of the present invention is to provide a process for the high yield and easy production of FBP and a purification process by which high purity FBP can be obtained easily with a high yield.

With the aim of overcoming the aforementioned problems involved in the art, the inventors of the present invention have conducted intensive studies and found an enzyme-aided process for the easy and large scale production of FBP and a purification process by which high purity FBP can be easily obtained. The present invention has been accomplished on the basis of these findings.

Particularly, in accordance with the present invention, a process for the production of FBP is provided, which comprises effecting reactions among F6P, ATP and a phosphate donor in the presence of the following enzymes (a) and (b):

(a) PFK 2, and (b) an enzyme which converts adenosine 5'-diphosphate (to be referred to as "ADP" hereinafter) into ATP.

Another object of the present invention is to provide a process for the production of FBP which comprises effecting reactions among glucose, ATP and a phosphate donor in the presence of the following enzymes (a), (b), (c) and (d):

(a) PFK 2, (b) an enzyme which converts ADP into ATP, (c) hexokinase or glucokinase, and (d) glucose 6-phosphate isomerase.

Still another object of the present invention is to provide a process for the production of FBP which comprises effecting reactions among fructose, ATP and a phosphate donor in the presence of the following enzymes (a), (b) and (c):

(a) PFK 2, (b) an enzyme which converts ADP into ATP, and (c) hexokinase or glucokinase.

Yet another object of the present invention is to provide a process for the production of FBP which comprises effecting reactions among glucose 6-phosphate, ATP and a phosphate donor in the presence of the following enzymes (a), (b) and (c):

(a) PFK 2, (b) an enzyme which converts ADP into ATP, and (c) glucose 6-phosphate isomerase.

A further object of the present invention is to provide a process for the production of FBP which comprises allowing diesterase to coexist in a solution containing fructose 1,2-cyclic, 6-bisphosphate.

A still further object of the present invention is to provide a process for the purification of FBP which comprises adding zinc salt to a solution containing FBP, removing formed precipitate of impurities and subsequently adding a zinc salt to the resulting solution to isolate formed precipitate of fructose 2,6-bisphosphate.

Other objects and advantages of the present invention will be made apparent as the description progresses.

the reaction mixture after hydrolysis by adding NaOH to FCP solution.

Figure 6:
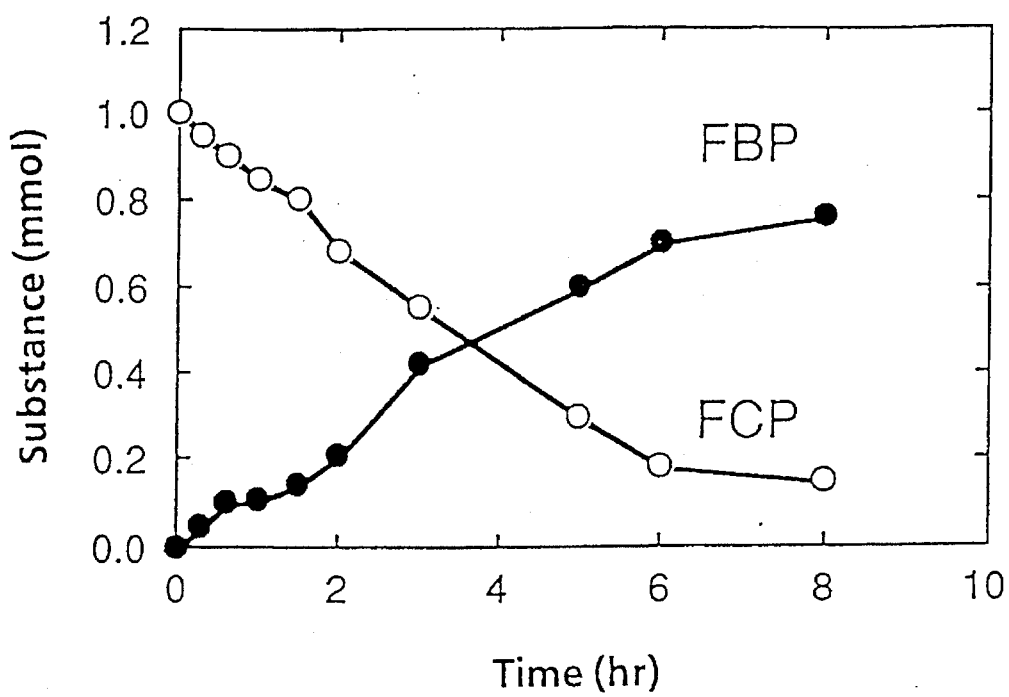

FIG. 6 is a graph showing a time course of FBP formation from FCP.

DETAILED DESCRIPTION OF THE INVENTION

FBP has been found as a minor component in animal tissues, and its importance as a carbohydrate metabolism-related factor has recently been recognized. FBP is a sugar phosphate compound represented by the following general formula:

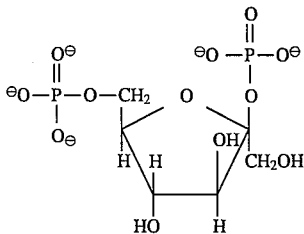

First, inventive processes for the production of FBP in which F6P, glucose, fructose or glucose 6-phosphate is used as the starting material are described. The definitions of one unit with respect to the enzyme which converts ADP into ATP, glucokinase and G6P are described in the section of Examples. 1. An inventive process for the production of FBP which comprises effecting reactions among F6P, ATP and a phosphate donor in the presence of the following enzymes (a) and (b):

(a) PFK 2, and (b) an enzyme which converts ADP into ATP.

When acetate kinase is used as the enzyme which converts ADP into ATP and acetyl phosphate is used as the phosphate donor, this process is effected in accordance with the following reaction formulae 1 and 2. That is, FBP and ADP are formed from F6P and ATP by the action of PFK 2 (formula 1), and the formed ADP reacts with acetyl phosphate and is converted into ATP by the action of acetate kinase (formula 2).

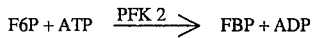 (formula 1)

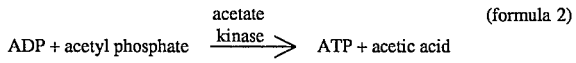 (formula 2)

2. An inventive process for the production of FBP which comprises effecting reactions among glucose, ATP and a phosphate donor in the presence of the following enzymes (a), (b), (c) and (d):

(a) PFK 2, (b) an enzyme which converts ADP into ATP, (c) hexokinase or glucokinase, and (d) glucose 6-phosphate isomerase.

When acetate kinase is used as the enzyme which converts ADP into ATP and acetyl phosphate is used as the phosphate donor, this process is effected in accordance with the following reaction formulae 3, 4, 1 and 2. That is, glucose 6-phosphate is formed from glucose and ATP by the action of hexokinase or glucokinase (formula 3), and the formed glucose 6-phosphate is converted into F6P by the action of glucose 6-phosphate isomerase (formula 4). Thereafter, the thus formed F6P is used in the aforementioned reactions of formulae 1 and 2.

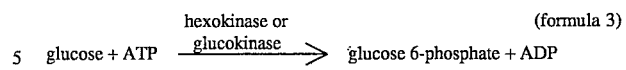 (formula 3)

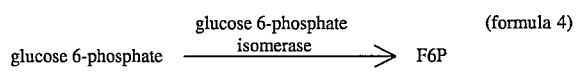 (formula 4)

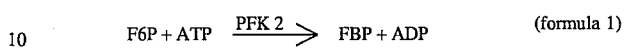 (formula 1)

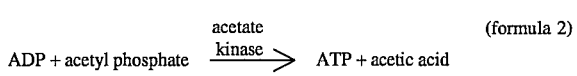 (formula 2)

3. An inventive process for the production of FBP which comprises effecting reactions among fructose, ATP and a phosphate donor in the presence of the following enzymes (a), (b) and (c):

(a) PFK 2, (b) an enzyme which converts ADP into ATP, and (c) hexokinase or glucokinase.

When acetate kinase is used as the enzyme which converts ADP into ATP and acetyl phosphate is used as the phosphate donor, this process is effected in accordance with the following reaction formulae 5, 1 and 2. That is, F6P is formed from fructose and ATP by the action of hexokinase or glucokinase (formula 5), and the thus formed F6P is used in the aforementioned reactions of formulae 1 and 2.

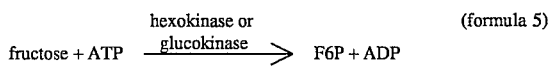 (formula 5)

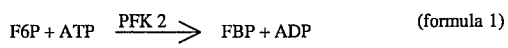 (formula 1)

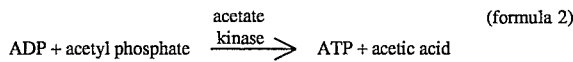 (formula 2)

4. An inventive process for the production of FBP which comprises effecting reactions among glucose 6-phosphate, ATP and a phosphate donor in the presence of the following enzymes (a), (b) and (c):

(a) PFK 2, (b) an enzyme which converts ADP into ATP, and (c) glucose 6-phosphate isomerase.

When pyruvate kinase is used as the enzyme which converts ADP into ATP and phosphoenolpyruvic acid is used as the phosphate donor, this process is effected in accordance with the following reaction formulae 4, 1 and 6. That is, glucose 6-phosphate is converted into F6P by the action of glucose 6-phosphate isomerase (formula 4), and FBP and ADP are formed from the thus formed F6P and ATP by the action of PFK 2 (formula 1). In addition, the thus formed ADP reacts with phosphoenolpyruvic acid and is converted into ATP by the action of pyruvate kinase (formula 6).

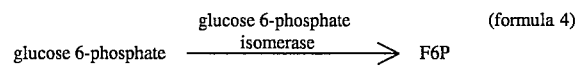 (formula 4)

 (formula 1)

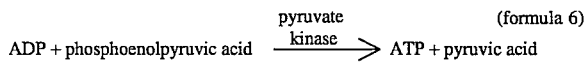 (formula 6)

The PFK 2 enzyme to be used in the FBP production process of the present invention may be of any type, provided that it has proper PFK 2 activity, such as a commercially available enzyme, a purified enzyme and a partially purified enzyme, as well as a microorganism or a tissue containing thereof and a disruption solution thereof. However, since the use of a microbial or tissue disruption solution sometimes causes decomposition of synthesized FBP, it is preferable to use a partially purified enzyme, more preferably a purified enzyme.

PFK 2 may be obtained from various origins with no particular limitation, such as rat tissues, fowl blood cells, sea bream muscles, barley seeds, tobacco leaves, soybean embryos, Saccharomyces cells, Aspergillus cells, Euglena cells, Trypanosoma cells and the like.

The amount of PFK 2 to be used also has no particular limitation and may be decided depending on the required amount of FBP. In a usual reaction system, it may be used in an amount of from 0.001 to 10,000 units per liter, preferably from 0.1 to 100 units per liter.

In the production process of the present invention, ATP is used as a phosphate source for the synthesis of FBP. The ATP used as a phosphate source is converted into ADP which can be reverted again to ATP by its reaction with an enzyme which converts ADP into ATP and a phosphate donor such as acetyl phosphate, phosphoenolpyruvic acid or the like. Such a process has rendered possible a reduction in the amount of the ATP, which is an expensive reactant, to a catalytically effective level.

The ADP-ATP converting enzyme to be used in the production process of the present invention may be of any type, provided that it can convert ADP into ATP, such as acetate kinase (E.C. 2.7.2.1), pyruvate kinase (E.C. 2.7.2.40) or the like.

The enzyme which converts ADP into ATP may be used in the form of a commercially available enzyme, a purified enzyme or a partially purified enzyme, as well as a microorganism or a tissue containing thereof or a disruption solution thereof. However, since the use of a microbial or tissue disruption solution sometimes causes decomposition of synthesized FBP, it is preferable to use a partially purified enzyme, more preferably a purified enzyme.

The enzyme which converts ADP into ATP may be obtained from various origins with no particular limitation, such as Saccharomyces cells, Aspergillus cells, Bacillus cells, Escherichia cells and the like.

Examples of the phosphate donor to be used in the production process of the present invention include acetyl phosphate, phosphoenolpyruvic acid and the like.

The phosphate donor may be of any type such as a commercially available phosphate donor, the phosphate donor isolated after synthesis, etc. A solution containing the phosphate donor may be used, and it is also possible to provide the phosphate donor by effecting another reaction to form the phosphate donor in the reaction solution for producing FBP.

In the process according to the present invention, acetyl phosphate is used as a phosphate donor when acetate kinase is used as an enzyme which converts ADP into ATP and phosphoenolpyruvic acid is used as a phosphate donor when the pyruvate kinase is used as an enzyme which converts ADP into ATP.

The amount of the aforementioned enzyme which converts ADP into ATP or the phosphate donor has no particular limitation and may be decided depending on the required amount of FBP. In a usual reaction system, the enzyme which converts ADP into ATP may be used in an amount of from 0,001 to 10,000 units per liter, preferably from 0.5 to 500 units per liter, and the phosphate donor may be used in an amount of from 0.01 to 500 equivalent, preferably from 1 to 50 equivalent, more preferably from 1 to 5 equivalent, to the required amount of FBP.

Further, the phosphate donor may be used in the range of from 0.01 to 500 moles, preferably 0.5 to 50 moles, and more preferably 0.5 to 5 moles per 1 mole of the substrate (i.e., F6P, glucose, G6P, or fructose).

The F6P to be used in the production process of the present invention may be of any type such as a commercially available F6P, F6P isolated after synthesis, etc. A solution containing F6P may be used, and it is also possible to provide F6P by effecting another reaction to form F6P in the reaction solution for producing FBP.

The amount of F6P to be used has no particular limitation and may be decided depending on the required amount of FBP. In a usual reaction system, it may be used in an amount of from 0.001 to 1,000 mmole per liter, preferably from 0.01 to 100 mmole per liter, more preferably from 0.1 to 10 mmole per liter.

The glucose to be used in the production process of the present invention may be of any type such as a commercially available glucose, glucose isolated after synthesis, etc. A solution containing glucose may be used, and it is also possible to provide glucose by effecting another reaction to form glucose in the reaction solution for producing FBP.

The amount of glucose to be used has no particular limitation and may be decided depending on the required amount of FBP. In a usual reaction system, it may be used in an amount of from 0.001 to 1,000 mmole per liter, preferably from 0.01 to 100 mmole per liter, more preferably from 0.1 to 10 mmole per liter.

Hexokinase (E.C. 2.7.1.1) or glucokinase (E.C. 2.7.1.2) and glucose 6-phosphate isomerase (E.C. 5.3.1.9) to be used in the production process of the present invention may be in the form of a commercially available enzyme, a purified enzyme or a partially purified enzyme, as well as a microorganism or a tissue containing such or a disruption solution thereof. However, since the use of a microbial or tissue disruption solution sometimes causes decomposition of synthesized FBP, it is preferable to use a partially purified enzyme, more preferably a purified enzyme.

Hexokinase or glucokinase and glucose 6-phosphate isomerase may be obtained from various origins with no particular limitation, such as Saccharomyces cells, Aspergillus cells, Bacillus cells, Escherichia cells and the like.

The amount of hexokinase or glucokinase and glucose 6-phosphate isomerase to be used has no particular limitation and may be decided depending on the required amount of FBP. In a usual reaction system, each of these enzymes may be used in an amount of from 0.001 to 10,000 units per liter, preferably from 0.1 to 100 units per liter.

In a usual reaction system, the ratio of the units of hexokinase or glucokinase to the units of glucose 6-phosphate isomerase may be in the range of from 1,000:1 to 1:1,000, preferably from 10:1 to 1:10.

The fructose to be used in the production process of the present invention may be of any type such as a commercially available fructose, fructose isolated after synthesis, etc. A solution containing fructose may be used, and it is also possible to provide fructose by effecting another reaction to form fructose in the reaction solution for producing FBP.

The amount of fructose to be used has no particular limitation and may be decided depending on the required amount of FBP. In a usual reaction system, it may be used in an amount of from 0.001 to 1,000 mmole per liter, preferably from 0.01 to 100 mmole per liter, more preferably from 0.1 to 10 mmole per liter.

The glucose 6-phosphate to be used in the production process of the present invention may be of any type such as a commercially available glucose 6-phosphate, glucose 6-phosphate isolated after synthesis, etc. A solution containing glucose 6-phosphate may be used, and it is also possible to provide glucose 6-phosphate by effecting another reaction to form glucose 6-phosphate in the reaction solution for producing FBP.

The amount of glucose 6-phosphate to be used has no particular limitation and may be decided depending on the required amount of FBP. In a usual reaction system, it may be used in an amount of from 0,001 to 1,000 mmole per liter, preferably from 0.01 to 100 mmole per liter, more preferably from 0.1 to 10 mmole per liter.

Next, another inventive process for the production of FBP in which diesterase is allowed to coexist in an FCP-containing solution is described.

The definition of one unit of diesterase is described in the section of Examples.

This process is effected in accordance with the following reaction formula 7 in which diesterase reacts with FCP to form FBP.

(formula 7)

Diesterase to be used in the FBP production process of the present invention has no particular limitation, provided that it has an FBP synthesizing activity, and may be in the form of a commercially available enzyme, a purified enzyme or a partially purified enzyme, as well as a microorganism or a tissue containing such or a disruption solution thereof. However, since the use of a microbial or tissue disruption solution sometimes causes decomposition of synthesized FBP, it is preferable to use a partially purified enzyme, more preferably a purified enzyme.

Diesterase may be obtained from various origins with no particular limitation, such as bovine heart, Crotalus venom and the like.

The amount of the diesterase to be used has no particular limitation and may be decided depending on the required amount of FBP. In a usual reaction system, it may be used in an amount of from 0.001 to 10,000 units per liter, preferably from 0.1 to 100 units per liter.

The FCP to be used in the production process of the present invention may be produced in accordance with the known method (cf., *European Journal of Biochemistry*, vol.117, p.319, 1981 and *Journal of Biological Chemistry*, vol.256, p.8679, 1981). The FCP synthesized by the known method may be used after isolation or a solution containing the synthesized FCP may be used. It is also possible to provide FCP by effecting another reaction to form FCP in the reaction solution for producing FBP. The amount of FCP to be used has no particular limitation and may be decided depending on the required amount of FBP. In a usual reaction system, it may be used in an amount of from 0.001 to 1,000 mmole per liter, preferably from 0.01 to 100 mmole per liter, more preferably from 0.1 to 10 mmole per liter.

In all of the aforementioned FBP production processes, divalent metal ions may be added to each reaction system in order to effect smooth reaction and, if required, monovalent metal ions may also be added. Examples of the divalent metal salt to provide divalent metal ions include magnesium chloride, magnesium sulfate, manganese chloride, zinc chloride, calcium chloride and the like and examples of the monovalent metal salt to provide monovalent metal ions include sodium chloride, potassium acetate, lithium chloride and the like.

As these metal salts, commercially available one, etc. may be used and the metal salt may be added to the reaction solution in the form of a powder or in the form of a solution.

The metal salt may be used alone or as a mixture of two or more. In a usual reaction system, metal ions may be used in the range of from 0.01 to 50 moles, preferably 0.1 to 10 moles, and more preferably 0.5 to 4 moles per 1 mole of the ATP used for the reaction. If required, however, the metal salt in an amount of from 0.1 to 10 moles per 1 mole of the substrate may further be added.

The reaction temperature may be in the range of from 0° to 80° C., preferably from 25° to 50° C. The reaction time has no particular limitation, provided that it is long enough to complete FBP production, but it may preferably be in the range of from 1 to 40 hours from a practical point of view.

Next, the FBP purification process of the present invention is described.

The zinc salt to be used in the purification process of the present invention may be of any type such as a commercially available zinc salts, etc. Examples of the zinc salt include zinc chloride, zinc acetate, and zinc sulfide, of which zinc chloride is preferable. The zinc salt may be added to the FBP-containing solution in the form of a powder or in the form of a solution.

This process comprises adding zinc salt to a solution containing FBP, removing formed precipitate of impurities and subsequently adding a zinc salt to the resulting solution to isolate the formed precipitate.

When an FBP-containing solution to be used in the purification process of the present invention is obtained by the aforementioned inventive FBP production process in which F6P, glucose, fructose or glucose 6-phosphate is used as a starting material, the amount of zinc salt firstly added to the FBP-containing solution may be in the range of from 0.5 to 2 moles per 1 mole of the remaining F6P. Through this treatment, any remaining F6P and free phosphate possibly formed by the decomposition of F6P and FBP are separated as precipitate.

After removing the thus formed precipitate, a second addition of zinc salt is carried out. In this case, zinc salt is added in at least the same molar amount with the FBP contained in the FBP-containing solution. Through this treatment, FBP is recovered as precipitate. The thus recovered precipitate of FBP zinc salt may be subjected to salt exchange, desalting and the like as the occasion demands.

Salt exchange, when an ion exchange resin is used for example, may be effected by various means such as a method in which the FBP zinc salt is firstly made into a free acid form using an anion exchange resin such as a DEAE-SEPHAROSE (Pharmacia); a method in which the zinc salt is converted directly into sodium salt using an Na type cation exchange resin; and a method in which the FBP zinc salt is firstly made into a free acid form using a cation exchange resin such as CM-SEPHAROSE (Pharmacia) and then converted into sodium salt or the like by titration or the like means.

Desalting may be effected, for example, by membrane filtration. Large scale desalting may be attained easily by the use of a reverse osmosis membrane system.

When an FBP-containing solution to be used in the purification process of the present invention is obtained by the inventive FBP production process in which diesterase is allowed to coexist in an FCP-containing solution, the amount of zinc salt firstly added to the FBP-containing solution may be in the range of from 0.2 to 2.5 moles, preferably 0.5 to 2 moles per 1 mole of FDP formed by the cleavage of FCP contained in the FBP-containing solution. By this treatment, FDP, FCP, free phosphate and F6P possibly formed by the decomposition of FBP and FDP are separated out as precipitate.

After removing the thus formed precipitate, a second addition of zinc salt is carried out. In this case, zinc salt is added in at least the same molar amount with the FBP contained in the FBP-containing solution. By this treatment, FBP is recovered as precipitate. The thus recovered precipitate of FBP zinc salt may be subjected to salt exchange, desalting and the like as the occasion demands.

Depending on the production conditions, however, complete removal of F6P and FDP as precipitate may not be effected by the aforementioned first zinc salt addition fractional precipitation. In that case, complete removal of the these impurities can be made by subjecting the filtrate resulting from the first zinc salt addition to an anion exchange resin. Though the anion exchange resin to be used for this purpose has no particular limitation provided that it has anion exchange groups, it may preferably have a small resin particle size and weakly basic exchange groups. Examples of this type of resin include DOWEX (Dow Chemical Co.), DIAION FP SERIES (Mitsubishi Kasei Corp.), AMBERLITE (Organo Co., Ltd.), DEAE-SEPHAROSE (Pharmacia) and the like. Usage and the amount of the resin and elution method may be decided in accordance with the instruction manual attached to each resin.

The following examples are provided to further illustrate the present invention. It is to be understood, however, that the examples are for purpose of illustration only and are not intended as a definition of the limits of the present invention.

EXAMPLES

Of the reagents used in the following examples, glucose and fructose in powder form and glucose 6-phosphate and F6P in the form of sodium salt were purchased from Ishizu Seiyaku Co., Ltd.

FCP was obtained in the powder form in accordance with the aforementioned method, by allowing dicyclohexyl carbodiimide (manufactured by Nacali Tasque) to react with FDP in pyridine (manufactured by Ishizu Seiyaku Co., Ltd.), effecting salt exchange of the thus formed FCP using DOWEX 50W cation exchange resin (manufactured by Dow Chemical Co.), making the product into sodium salt using a sodium hydroxide aqueous solution and then drying the sodium salt to obtain the FCP powder of interest.

Acetyl phosphate in the form of lithium potassium acetyl phosphate and phosphoenolpyruvic acid in the form of trisodium phosphoenolpyruvate were purchased from Nacali Tasque.

Other reagents used are all commercial articles.

PFK 2 for use in the following examples was obtained in accordance with the procedure of J. Francois, E. Van Schaftingen and H. G. Hers et al. (*European Journal of Biochemistry*, vol.145, p.187, 1984), by subjecting a yeast extract prepared from a commercial yeast strain (ORIENTAL YEAST, manufactured by Oriental Yeast Co., Ltd.) to a DEAE-SEPHAROSE column chromatography and a BLUE-SEPHAROSE column chromatography and concentrating the thus partially purified product. One unit of PFK 2 is defined as the amount of enzyme which synthesizes 1 µmole of FBP per 1 minute from F6P and ATP. In this case, determination of FBP was carried out by comparing its peak height obtained by an HPLC-aided sugar detection method which will be described later with a peak height of FBP sodium salt powder manufactured by Sigma Chemical Co.

Acetate kinase, glucokinase, glucose 6-phosphate isomerase and pyruvate kinase were purchased from Unitika, Ltd., and hexokinase from BMY. Units of these enzymes described in the manufacturers's instructions were used as such.

As the diesterase to be used in the following examples, phosphodiesterase (bovine and snake origins), nuclease P1, ribonuclease A and deoxyribonuclease I were purchased from BMY. One unit of the diesterase is defined as the amount of the enzyme which synthesizes 1 µmole of FBP per 1 minute from FCP. In this case, determination of FBP was carried out by comparing its peak height obtained by the following HPLC-aided 'sugar detection method with a peak height of FBP sodium salt powder manufactured by Sigma Chemical Co.

Detection of sugars including FBP was carried out using an HPLC system equipped with an LC MODULE 1 (Waters Associates, Inc.) and a 410 differential refractometer. CHEMCOPACK NUCLEOSIL (4.6×250 mm, manufactured by Chemco) was used as an analytical column. As to a mobile phase, 50 mM ammonium acetate solution was used at a rate of 0.5 ml/min.

EXAMPLE 1 AND COMPARATIVE EXAMPLE 1

F6P, acetyl phosphate, ATP, PFK 2 and acetate kinase to their respective final concentrations shown in Table 1 and magnesium chloride in a twice molar amount based on the added ATP were added to HEPES buffer (50 mmole per liter, pH 7.0). A 100 ml portion of the thus prepared buffer solution was incubated at 37° C. for 8 hours, and FBP in the buffer solution was determined at intervals (reactions 2 to 5). As a comparative example, F6P, ATP and PFK 2 were added to HEPES buffer (50 mmole per liter, pH 7.0) to their respective final concentrations shown in Table 1. A 100 ml portion of the thus prepared buffer solution was incubated at 37° C. for 8 hours, and FBP in the buffer solution was determined at intervals (Comparative Example 1, reaction 1). Results of these experiments are collectively shown in FIG. 1.

TABLE 1

| Enzymatic synthesis of FBP from F6P | | | | | |
|---|---|---|---|---|---|
| F6P (mmole/l) | ATP (mmole/l) | Acetyl phosphate (mmole/l) | PFK 2 (unit/l) | Acetate kinase (unit/l) | FBP yield (%) |
| Reaction 1 | 1 | 2 | — | 10 | — | 12 |
| Reaction 2 | 1 | 0.02 | 3 | 10 | 10 | 81 |
| Reaction 3 | 2 | 0.02 | 6 | 20 | 10 | 80 |
| Reaction 4 | 5 | 0.05 | 15 | 50 | 20 | 75 |
| Reaction 5 | 10 | 0.05 | 30 | 100 | 50 | 77 |

Figure 1:
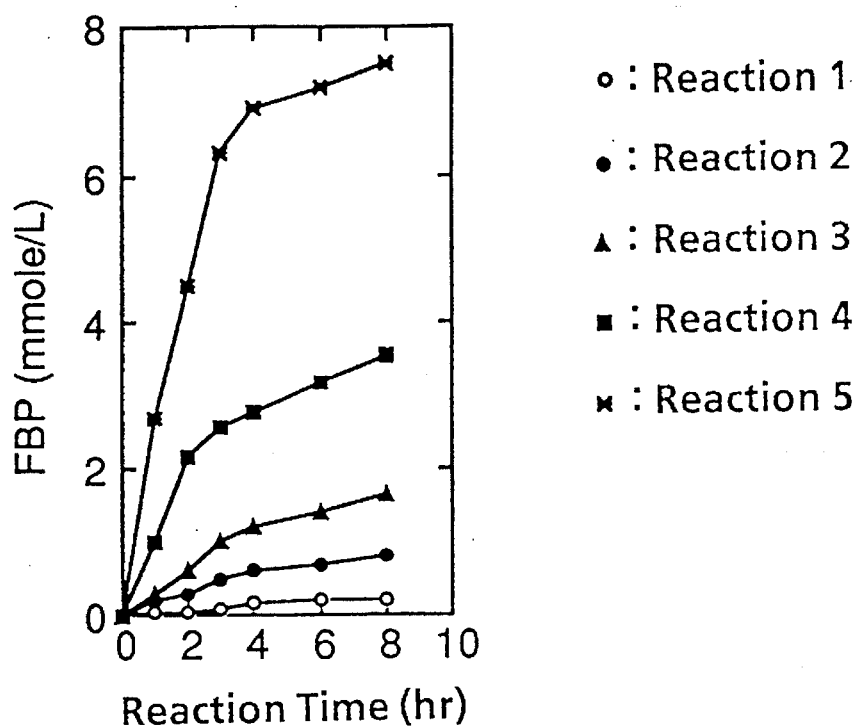
FIG. 1 is a graph showing time courses of FBP formation under various reaction conditions.

Results of reactions 1 and 2 shown in FIG. 1 indicate that FBP can be synthesized efficiently with a high conversion ratio when acetate kinase, an enzyme which converts ADP into ATP, and acetyl phosphate, a phosphate donor, are added to the reaction solution, in comparison with the comparative example in which these reagents are not used but a 100 times larger amount of ATP is used. In addition, the results of the reactions 2 to 5 show that FBP can be synthesized efficiently within greatly varied concentration ranges of the added substances and enzymes.

EXAMPLE 2 AND COMPARATIVE EXAMPLE 2

PFK 2 (final concentration: 10 units per liter) and acetate kinase (final concentration: 50 units per liter) were added to 100 ml of HEPES buffer (50 mmole per liter, pH 7.0)

containing 1 mmole per liter of F6P, 3 mmole per liter of acetyl phosphate and 0.2 mmole per liter of ATP, followed by hours of reaction at 37° C. As a comparative example, PFK 2 (final concentration: 10 units per liter) was added to 100 ml of HEPES buffer (50 mmole per liter, pH 7.0) containing 1 mmole per liter of F6P and 2 mmole per liter of ATP, followed by 8 hours of reaction at 37° C. (conventional process, Comparative Example 2). Results of these experiments are shown in FIG. 2.

Figure 2:
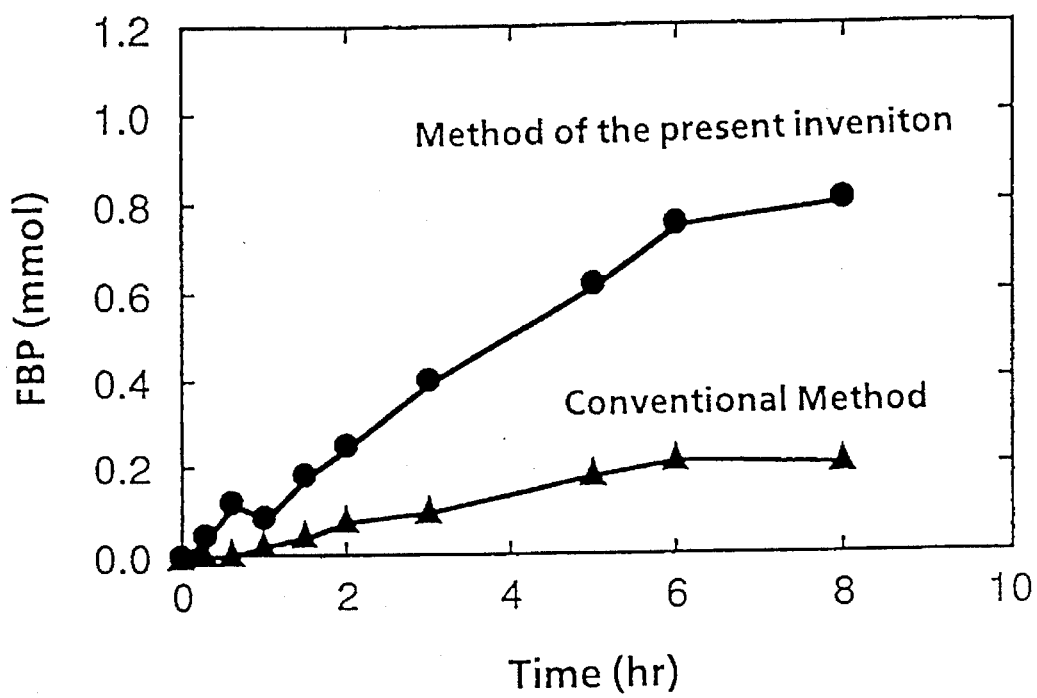
FIG. 2 is a graph showing time courses of FBP formation by the present and prior reaction methods.

As is evident from the results shown in FIG. 2, FBP can be synthesized efficiently with a high conversion ratio when acetate kinase, an enzyme which converts ADP into ATP, and acetyl phosphate, a phosphate donor, are added to the reaction solution, in comparison with the comparative example in which these reagents are not used but 10 times larger amount of ATP is used.

EXAMPLE 3

F6P, acetyl phosphate, ATP, PFK 2 and acetate kinase to their respective final concentrations shown in Table 2 and magnesium chloride in a twice molar amount based on the added ATP were added to HEPES buffer (50 mmole per liter, pH 7.5). A 10 ml portion of the thus prepared buffer solution was incubated at 37° C. for an appropriate period (maximum 33 hours), and FBP in the buffer solution was determined. Yield of FBP based on the initial amount of F6P was calculated. Results of these experiments are collectively shown in Table 2.

EXAMPLE 4

PFK 2 (final concentration: 20 units per liter), acetate kinase (final concentration: 100 units per liter), glucokinase (final concentration: 20 units per liter) and glucose 6-phosphate isomerase (final concentration: 20 units per liter) were added to 100 ml of HEPES buffer (50 mmole per liter, pH 7.0) containing 2 mmole per liter of glucose, 3 mmole per liter of acetyl phosphate and 0.2 mmole per liter of ATP, followed by 8 hours of reaction at 37° C. Results of this experiment are shown in FIG. 3.

Figure 3:
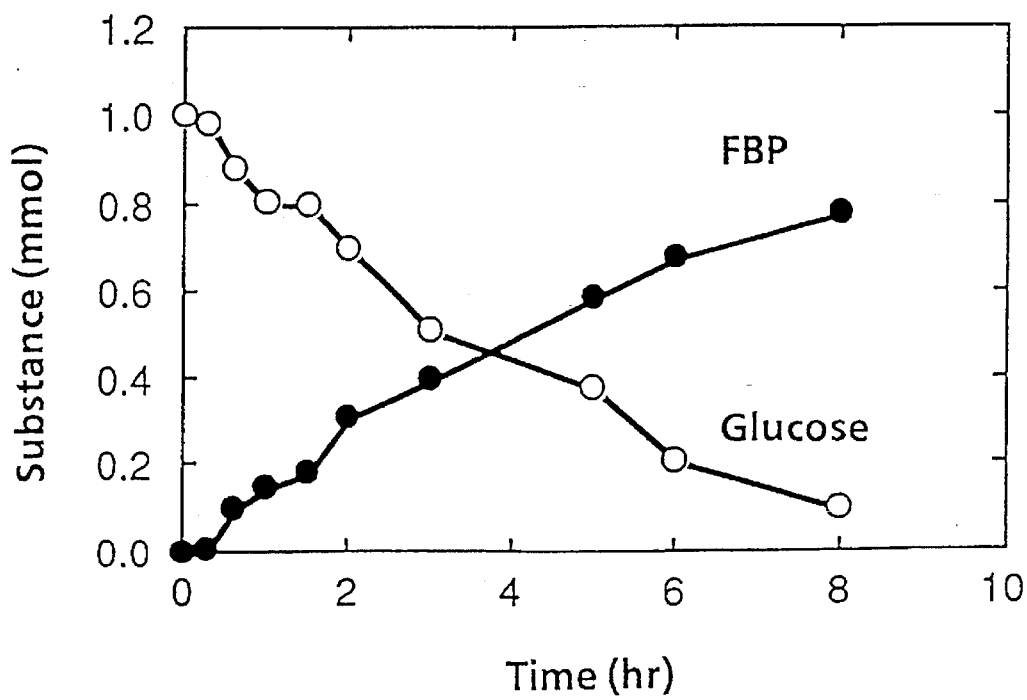
FIG. 3 is a graph showing a time course of FBP formation from glucose.

As is evident from the results shown in FIG. 3, FBP can be synthesized by the process of the present invention even when glucose is used as a starting material.

EXAMPLE 5

Glucose, acetyl phosphate or phosphoenolpyruvic acid, ATP, PFK 2, acetate kinase or pyruvate kinase, glucose 6-phosphate isomerase and hexokinase or glucokinase to their respective final concentrations shown in Table 3 and magnesium chloride in a twice molar amount based on the added ATP were added to HEPES buffer (50 mmole per liter, pH 7.5). A 10 ml portion of the thus prepared buffer solution was incubated at 37° C. for an appropriate period (maximum 22 hours), and FBP in the buffer solution was determined. Yield of FBP based on the initial amount of glucose was calculated. Results of these experiments are collectively shown in Table 3.

TABLE 2

Enzymatic synthesis of FBP from F6P

| F6P (mmole/l) | ATP (mmole/l) | Acetyl phosphate (mmole/l) | PFK 2 (unit/l) | Acetate kinase (unit/l) | Reaction time (hr) | FBP yield (%) |
|---|---|---|---|---|---|---|
| 0.1 | 0.02 | 0.5 | 1 | 5 | 8 | 88 |
| 1 | 0.02 | 3 | 3 | 5 | 18 | 75 |
| 2 | 0.5 | 10 | 3 | 5 | 30 | 58 |
| 5 | 0.05 | 10 | 15 | 20 | 33 | 62 |
| 10 | 0.5 | 30 | 100 | 50 | 6 | 78 |

As is evident from the results shown in Table 2, FBP can be synthesized efficiently within greatly varied concentration ranges of the added substances and enzymes.

TABLE 3

Enzymatic synthesis of FBP from glucose

| Glucose (mmole/l) | ATP (mmole/l) | Acetyl Phosphate (mmole/l) | Phosphoenolpyruvic acid (mmole/l) | PFK 2 (unit/l) | Acetate kinase (unit/l) | Pyruvate kinase (unit/l) | Gluco-kinase (unit/l) | Hexo-kinase (unit/l) | Glucose 6-phosphate isomerase (unit/l) | Reaction time (hr) | FBP yield (%) |
|---|---|---|---|---|---|---|---|---|---|---|---|
| 0.1 | 0.02 | 0.5 | — | 1 | 5 | — | 5 | — | 5 | 8 | 84 |
| 1 | 0.02 | 3 | — | 10 | 5 | — | 50 | — | 5 | 8 | 66 |
| 5 | 0.1 | 10 | — | 50 | 5 | — | 5 | — | 50 | 20 | 62 |
| 10 | 0.5 | 31 | — | 100 | 50 | — | 50 | — | 50 | 20 | 64 |
| 0.1 | 0.02 | — | 0.5 | 1 | — | 5 | — | 5 | 5 | 22 | 65 |
| 1 | 0.02 | — | 3 | 10 | — | 50 | — | 50 | 50 | 22 | 62 |
| 5 | 0.1 | — | 10 | 50 | — | 50 | — | 50 | 50 | 22 | 59 |
| 10 | 0.5 | — | 31 | 100 | — | 50 | — | 50 | 50 | 22 | 55 |
| 1 | 0.5 | — | 31 | 100 | — | 50 | 50 | — | 50 | 17 | 71 |
| 1 | 0.5 | 31 | — | 100 | 50 | — | — | 50 | 50 | 17 | 68 |

As is evident from the results shown in Table 3, FBP can be synthesized efficiently within greatly varied concentration ranges of the added substances and enzymes.

EXAMPLE 6

PFK 2 (final concentration: 10 units per liter), acetate kinase (final concentration: 100 units per liter) and glucokinase (final concentration: 20 units per liter) were added to 100 ml of HEPES buffer (50 mmole per liter, pH 7.0) containing 2 mmole per liter of fructose, 3 mmole per liter of acetyl phosphate and 0.1 mmole per liter of ATP, followed by 8 hours of reaction at 37° C. Results of these experiments are shown in FIG. 4.

Figure 4:
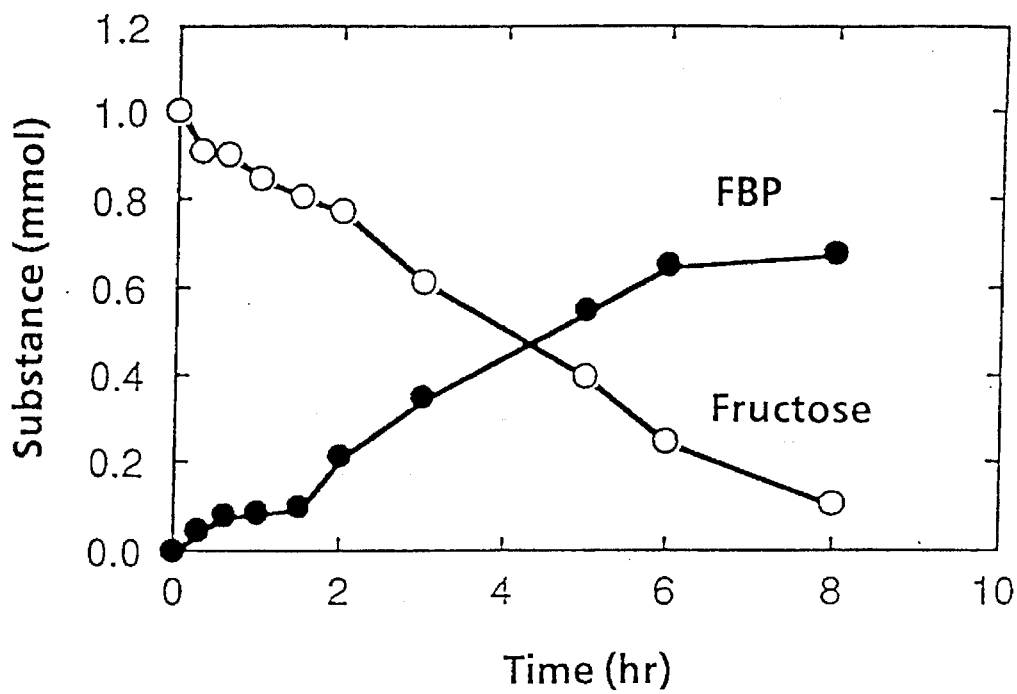
FIG. 4 is a graph showing a time course of FBP formation from fructose.

As is evident from the results shown in FIG. 4, FBP can be synthesized by the process of the present invention even when fructose is used as a starting material.

EXAMPLE 7

Fructose, acetyl phosphate or phosphoenolpyruvic acid, ATP, PFK 2, acetate kinase or pyruvate kinase and hexokinase or glucokinase to their respective final concentrations shown in Table 4 and magnesium chloride in a 3 times molar amount based on the added ATP were added to Tris buffer (50 mmole per liter, pH 7.5). A 10 ml portion of the thus prepared buffer solution was incubated at 37° C. for an appropriate period (maximum 22 hours), and FBP in the buffer solution was determined. Yield of FBP based on the initial amount of fructose was calculated. Results of these experiments are collectively shown in Table 4.

EXAMPLE 8

Glucose 6-phosphate, acetyl phosphate or phosphoenolpyruvic acid, ATP, PFK 2, acetate kinase or pyruvate kinase and glucose 6-phosphate isomerase to their respective final concentrations shown in Table 5 and magnesium chloride in the same molar amount with the added ATP were added to Tris buffer (50 mmole per liter, pH 7.5). A 10 ml portion of the thus prepared buffer solution was incubated at 37° C. for an appropriate period, and FBP in the buffer solution was determined. Yield of FBP based on the initial amount of glucose 6-phosphate was calculated. Results of these experiments are collectively shown in Table 5.

TABLE 4

| | | | | Enzymatic synthesis of FBP from fructose | | | | | | |
|---|---|---|---|---|---|---|---|---|---|---|
| Fructose (mmole/l) | ATP (mmole/l) | Acetyl Phosphase (mmole/l) | Phosphoenolpyruvic acid (mmole/l) | PFK 2 (unit/l) | Acetate kinase (unit/l) | Pyruvate kinase (unit/l) | Glucokinase (unit/l) | Hexokinase (unit/l) | Reaction time (hr) | FBP yield (%) |
| 0.1 | 0.02 | 0.5 | — | 1 | 5 | — | 5 | — | 8 | 80 |
| 1 | 0.02 | 3 | — | 10 | 5 | — | 50 | — | 8 | 71 |
| 5 | 0.1 | 10 | — | 50 | 5 | — | 5 | — | 20 | 65 |
| 10 | 0.5 | 30 | — | 100 | 50 | — | 50 | — | 20 | 62 |
| 0.1 | 0.02 | — | 0.5 | 1 | — | 5 | — | 5 | 22 | 66 |
| 1 | 0.02 | — | 3 | 10 | — | 50 | — | 50 | 22 | 60 |
| 5 | 0.1 | — | 10 | 50 | — | 50 | — | 50 | 22 | 62 |
| 10 | 0.5 | — | 30 | 100 | — | 50 | — | 50 | 22 | 58 |
| 1 | 0.5 | — | 30 | 100 | — | 50 | 50 | — | 17 | 64 |
| 1 | 0.5 | 30 | — | 100 | 50 | — | — | 50 | 17 | 66 |

As is evident from the results shown in Table 4, FBP can be synthesized efficiently within greatly varied concentration ranges of the added substances and enzymes.

TABLE 5

| | | | | Enzymatic synthesis of FBP from glucose 6-phosphate | | | | | |
|---|---|---|---|---|---|---|---|---|---|
| Glucose 6-phosphate (mmole/l) | ATP (mmole/l) | Acetyl Phosphase (mmole/l) | Phosphoenolpyruvic acid (mmole/l) | PFK 2 (unit/l) | Acetate kinase (unit/l) | Pyruvate kinase (unit/l) | Glucose 6-phosphate isomerase (unit/l) | Reaction time (hr) | FBP yield (%) |
| 0.1 | 0.02 | 0.5 | — | 1 | 5 | — | 5 | 18 | 88 |
| 1 | 0.02 | 3 | — | 3 | 5 | — | 5 | 18 | 75 |
| 5 | 0.05 | 10 | — | 15 | 20 | — | 20 | 18 | 62 |
| 10 | 0.5 | 31 | — | 100 | 50 | — | 50 | 18 | 51 |
| 0.1 | 0.02 | — | 0.5 | 1 | — | 5 | 5 | 18 | 75 |

TABLE 5-continued

| Enzymatic synthesis of FBP from glucose 6-phosphate | | | | | | | | | |
|---|---|---|---|---|---|---|---|---|---|
| Glucose 6-phosphate (mmole/l) | ATP (mmole/l) | Acetyl Phosphate (mmole/l) | Phospho-enolpyruvic acid (mmole/l) | PFK 2 (unit/l) | Acetate kinase (unit/l) | Pyruvate kinase (unit/l) | Glucose 6-phosphate isomerase (unit/l) | Reaction time (hr) | FBP yield (%) |
| 1 | 0.02 | — | 3 | 3 | — | 5 | 5 | 18 | 73 |
| 5 | 0.05 | — | 10 | 15 | — | 20 | 20 | 18 | 62 |
| 10 | 0.5 | — | 30 | 100 | — | 50 | 50 | 18 | 65 |

As is evident from the results shown in Table 5, FBP can be synthesized efficiently within greatly varied concentration ranges of the added substances and enzymes.

EXAMPLE 9

100 ml of phosphate buffer (50 mmole per liter, pH 7.0) containing 5 mmole per liter of FCP, 10 mmole per liter of magnesium chloride and 20 units per liter of snake phosphodiesterase as a diesterase was incubated at 28° C. for 8 hours, and the resulting reaction solution was analyzed by HPLC. Results of this experiment are shown in FIG. 5(A). FIG. 5(B) shows results of an HPLC analysis of a solution containing 1 mmole per liter each of FBP, FCP and FDP purchased from Sigma Chemical Co. FIG. 5(C) shows results of a comparative example in which NaOH was added to an aqueous solution containing 5 mmole per liter of FCP and, after 3 hours of standing, the resulting solution was neutralized with HCl and subjected to HPLC analysis.

Figure 5:
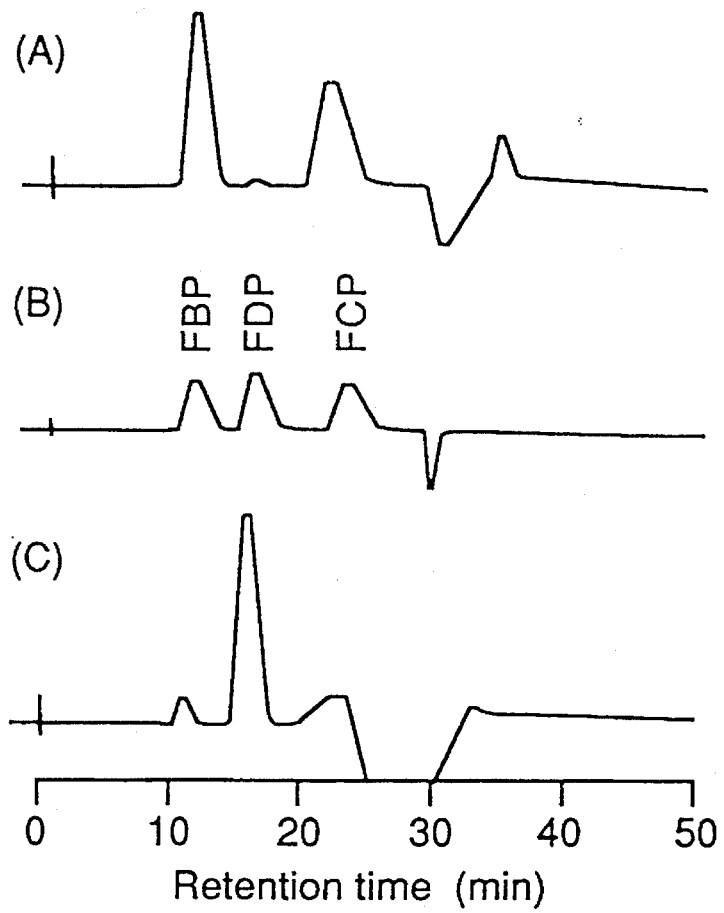
FIG. 5(A),5(B),5(C) are chromatographic profiles, 5(A): the reaction mixture of FBP after 8h reaction; 5(B): the solution containing 1 mM each of FBP, FCP and FDP; 5(C)

As is evident from the results shown in FIG. 5, FBP can be synthesized directly from FCP with high efficiency by the use of phosphodiesterase.

EXAMPLE 10

Diesterase was added to 100 ml of HEPES buffer (50 mmole per liter, pH 7.0) containing 1 mmole per liter of FCP to a final concentration of 20 units per liter, followed by 8 hours of reaction at 37° C. Results of this experiment are shown in FIG. 6.

As is evident from the results shown in FIG. 6, FBP can be synthesized directly from FCP with high efficiency by the use of diesterase.

EXAMPLE 11

FCP and diesterase (bovine phosphodiesterase, nuclease P1, ribonuclease A or deoxyribonuclease I) to their respective final concentrations shown in Table 6 and magnesium chloride in a twice molar amount based on the added FCP were added to phosphate buffer (50 mmole per liter, pH 7.0). A 10 ml portion of the thus prepared buffer solution was incubated at 32° C. for 16 hours and then subjected to HPLC analysis to calculate yield of FBP based on the initial amount of FCP. Results of this experiment are shown in Table 6.

TABLE 6

| Enzymatic synthesis of FBP from FCP | | |
|---|---|---|
| Diesterase (unit/l) | FCP (mmole/l) | FBP yield (%) |
| Bovine phosphodiesterase | | |
| 1 | 0.5 | 65 |

TABLE 6-continued

| Enzymatic synthesis of FBP from FCP | | |
|---|---|---|
| Diesterase (unit/l) | FCP (mmole/l) | FBP yield (%) |
| 10 | 0.5 | 55 |
| 102 | 5 | 54 |
| Nuclease P1 | | |
| 1 | 0.5 | 28 |
| 10 | 0.5 | 40 |
| 98 | 5 | 31 |
| Ribonuclease A | | |
| 1 | 0.5 | 18 |
| 10 | 4.5 | 25 |
| 101 | 4.5 | 15 |
| Deoxyribonuclease I | | |
| 1 | 0.5 | 45 |
| 10 | 4.5 | 58 |
| 100 | 4.5 | 51 |

As is evident from the results shown in Table 6, FBP can be synthesized directly from FCP with high efficiency in all cases by the use of phosphodiesterase.

EXAMPLE 12

Fractional precipitation of FBP was carried out by adding zinc chloride to the FBP-containing solution which has been obtained in Example 9 by allowing phosphodiesterase to react with FCP. That is, zinc chloride powder was added to ml of the FBP-containing solution to a final concentration of 2 mmole per liter. After 90 minutes of stirring at room temperature, the thus formed precipitate was removed by filtration. Zinc chloride powder was added to the resulting filtrate to a final concentration of 8 mmole per liter. After 90 minutes of stirring at room temperature, the thus formed precipitate was collected by filtration. The results are shown in Table 7.

TABLE 7

| Purification of FBP by the addition of zinc chloride | | | | | | |
|---|---|---|---|---|---|---|
| | Total zinc chloride added (mmole/l) | Residual components in filtrate (upside, mmole/l; down side, %) | | | | |
| | | Free $PO_4^{2-}$ | F6P | FDP | FCP | FBP |
| | 0 | trace | trace | 0.11 | 1.80 | 2.99 |
| | | — | — | 100 | 100 | 100 |
| First addition | 0.2 | 0.04 | 0.04 | 0.08 | 1.80 | 0.02 |
| | | — | — | 81 | 105 | 1 |
| Second | 3.00 | 0 | 0 | trace | trace | 1.98 |

TABLE 7-continued

Purification of FBP by the addition of zinc chloride

| Total zinc chloride added (mmole/l) | Residual components in filtrate (upside, mmole/l; down side, %) | | | | |
|---|---|---|---|---|---|
| | Free $PO_4^{2-}$ | F6P | FDP | FCP | FBP |
| addition | — | — | 0 | 0 | 65 |

On the basis of the results shown in Table 7, it is evident that the precipitate formed by the first addition of zinc chloride comprises free phosphate FCP, as well as FDP and F6P both of which seem to be generated by the decomposition of FCP, and that high purity FBP can be obtained easily by collecting the precipitate formed by the second addition of zinc chloride.

EXAMPLE 13

Fractional precipitation of FBP was carried out by adding zinc chloride to the FBP-containing solution which has been obtained in Example 2. That is, 0.2 mmol of zinc chloride powder was added to 100 ml of the FBP-containing solution. After 30 minutes of stirring at room temperature, the thus formed precipitate was removed by filtration. To the resulting filtrate was again added 2.8 mmol of zinc chloride powder. After 30 minutes of stirring at room temperature, the thus formed precipitate was collected by filtration. The results are shown in Table 8.

TABLE 8

Purification of FBP by the addition of zinc chloride

| | Total zinc chloride added (mmole/l) | Residual components in filtrate (upside, mmole/l; down side, %) | | |
|---|---|---|---|---|
| | | Free $PO_4^{2-}$ | F6P | FBP |
| | 0 | 0.05 | 0.13 | 0.81 |
| | | 100 | 100 | 100 |
| First addition | 0.20 | 0.04 | 0.14 | 0.02 |
| | | 88 | 105 | 2 |
| Second addition | 3.00 | trace | trace | 0.60 |
| | | 0 | 0 | 74 |

On the basis of the results shown in Table 8, it is evident that the precipitate formed by the first addition of zinc chloride comprises free phosphate and F6P and that high purity FBP can be obtained easily by collecting the precipitate formed by the second addition of zinc chloride. Thus, according to the present invention, FBP can be produced easily with a high yield and high purity FBP can be obtained easily.

While the invention has been described in detail and with reference to specific examples thereof, it will be apparent to one skilled in the art that various changes and modifications can be made therein without departing from the spirit and scope thereof.

What is claimed is:

1. A process for producing fructose 2,6-bisphosphate comprising the steps of:

admixing fructose 6-phosphate, adenosine 5'-triphosphate, a phosphate donor, and the following enzymes (a) and (b):

(a) fructose 6-phosphate 2-kinase, and (b) an enzyme which converts adenosine 5'-diphosphate into adenosine 5'-triphosphate, in a reaction buffer, allowing enzymatic reaction to occur so as to form fructose 2,6-bisphosphate, and isolating said fructose 2,6-bisphosphate from the resulting reaction buffer.

2. The process for producing fructose 2,6-bisphosphate according to claim 1, wherein said enzyme which converts adenosine 5'-diphosphate into adenosine 5'-triphosphate is acetate kinase and said phosphate donor is acetyl phosphate.

3. The process for producing fructose 2,6-bisphosphate according to claim 1, wherein said enzyme which converts adenosine 5'-diphosphate into adenosine 5'-triphosphate is pyruvate kinase and said phosphate donor is phosphoenolpyruvic acid.

4. A process for producing fructose 2,6-bisphosphate comprising the steps of:

admixing glucose, adenosine 5'-triphosphate, a phosphate donor and the following enzymes (a), (b), (c) and (d):

(a) fructose 6-phosphate 2-kinase, (b) an enzyme which converts adenosine 5'-diphosphate into adenosine 5'-triphosphate, (c) hexokinase or glucokinase, and (d) glucose 6-phosphate isomerase, in a reaction buffer, allowing enzymatic reaction to occur so as to form fructose 2,6-bisphosphate, and isolating said fructose 2,6-bisphosphate from the resulting reaction buffer.

5. The process for producing fructose 2,6-bisphosphate according to claim 4, wherein said enzyme which converts adenosine 5'-diphosphate into adenosine 5'-triphosphate is acetate kinase and said phosphate donor is acetyl phosphate.

6. The process for producing fructose 2,6-bisphosphate according to claim 4, wherein said enzyme which converts adenosine 5'-diphosphate into adenosine 5'-triphosphate is pyruvate kinase and said phosphate donor is phosphoenolpyruvic acid.

7. A process for producing fructose 2,6-bisphosphate comprising the steps of:

admixing fructose, adenosine 5'-triphosphate, a phosphate donor and the following enzymes (a), (b) and (c):

(a) fructose 6-phosphate 2-kinase, (b) an enzyme which converts adenosine 5'-diphosphate into adenosine 5'-triphosphate, and (c) hexokinase or glucokinase, in a reaction buffer, allowing enzymatic reaction to occur so as to form fructose 2,6-bisphosphate, and isolating said fructose 2,6-bisphosphate from the resulting reaction buffer.

8. The process for producing fructose 2,6-bisphosphate according to claim 7, wherein said enzyme which converts adenosine 5'-diphosphate into adenosine 5'-triphosphate is acetate kinase and said phosphate donor is acetyl phosphate.

9. The process for producing fructose 2,6-bisphosphate according to claim 7, wherein said enzyme which converts adenosine 5'-diphosphate into adenosine 5'-triphosphate is pyruvate kinase and said phosphate donor is phosphoenolpyruvic acid.

10. A process for producing fructose 2,6-bisphosphate comprising the steps of:

admixing glucose 6-phosphate, adenosine 5'-triphosphate, a phosphate donor and the following enzymes (a), (b) and (c):

(a) fructose 6-phosphate 2-kinase, (b) an enzyme which converts adenosine 5'-diphosphate into adenosine 5'-triphosphate, and (c) glucose 6-phosphate isomerase, in a reaction buffer, allowing enzymatic reaction to take place so as to form fructose 2,6-bisphosphate, and isolating said fructose 2,6-bisphosphate from the resulting reaction buffer.

11. The process for producing fructose 2,6-bisphosphate according to claim 10, wherein said enzyme which converts adenosine 5'-diphosphate into adenosine 5'-triphosphate is acetate kinase and said phosphate donor is acetyl phosphate.

12. The process for producing fructose 2,6-bisphosphate according to claim 10, wherein said enzyme which converts adenosine 5'-diphosphate into adenosine 5'-triphosphate is pyruvate kinase and said phosphate donor is phosphoenolpyruvic acid.

13. The process for producing fructose 2,6-bisphosphate according to claim 1, wherein isolating said fructose 2,6-bisphosphate from the resulting reaction buffer is carried out by the steps comprising:

adding a zinc salt to the reaction buffer containing fructose 2,6-bisphosphate to form a precipitate of impurities, removing said precipitate from the resulting solution, further adding a zinc salt to the resulting solution to form a precipitate of fructose 2,6-bisphosphate, recovering said precipitate from the resulting solution to form purified fructose 2,6-bisphosphate.

14. The process for producing fructose 2,6-bisphosphate according to claim 13, wherein said zinc salt is zinc chloride.

15. The process for producing fructose 2,6-bisphosphate according to claim 4, wherein isolating said fructose 2,6-bisphosphate from the resulting reaction buffer is carried out by the steps comprising:

adding a zinc salt to the reaction buffer containing fructose 2,6-bisphosphate to form a precipitate of impurities, removing said precipitate from the resulting solution, further adding a zinc salt to the resulting solution to form a precipitate of fructose 2,6-bisphosphate, recovering said precipitate from the resulting solution to form purified fructose 2,6-bisphosphate.

16. The process for producing fructose 2,6-bisphosphate according to claim 15, wherein said zinc salt is zinc chloride.

17. The process for producing fructose 2,6-bisphosphate according to claim 7, wherein isolating said fructose 2,6-bisphosphate from the resulting reaction buffer is carried out by the steps comprising:

adding a zinc salt to the reaction buffer containing fructose 2,6-bisphosphate to form a precipitate of impurities, removing said precipitate from the resulting solution, further adding a zinc salt to the resulting solution to form a precipitate of fructose 2,6-bisphosphate, recovering said precipitate from the resulting solution to form purified fructose 2,6-bisphosphate.

18. The process for producing fructose 2,6-bisphosphate according to claim 17, wherein said zinc salt is zinc chloride.

19. The process for producing fructose 2,6-bisphosphate according to claim 10, wherein isolating said fructose 2,6-bisphosphate from the resulting reaction buffer is carried out by the steps comprising:

adding a zinc salt to the reaction buffer containing fructose 2,6-bisphosphate to form a precipitate of impurities, removing said precipitate from the resulting solution, further adding a zinc salt to the resulting solution to form a precipitate of fructose 2,6-bisphosphate, recovering said precipitate from the resulting solution to form purified fructose 2,6-bisphosphate.

20. The process for producing fructose 2,6-bisphosphate according to claim 19, wherein said zinc salt is zinc chloride.

* * * * *